US010806692B2

(12) United States Patent
Guskey et al.

(10) Patent No.: US 10,806,692 B2
(45) Date of Patent: Oct. 20, 2020

(54) SKIN CLEANSING COMPOSITIONS COMPRISING COLOR STABLE ABRASIVE PARTICLES

(71) Applicant: The Procter & Gamble Company, Cincinnati, OH (US)

(72) Inventors: Gerald John Guskey, Symmes Township, OH (US); Shannon Dale Wagers, Liberty Township, OH (US); Somil Manjul Shah, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 363 days.

(21) Appl. No.: 15/283,706

(22) Filed: Oct. 3, 2016

(65) Prior Publication Data

US 2018/0092831 A1 Apr. 5, 2018

(51) Int. Cl.
| | |
|---|---|
| *A61K 8/92* | (2006.01) |
| *A61K 8/25* | (2006.01) |
| *A61K 8/02* | (2006.01) |
| *A61K 8/362* | (2006.01) |
| *A61K 8/368* | (2006.01) |
| *A61Q 19/10* | (2006.01) |

(52) U.S. Cl.
CPC .............. *A61K 8/92* (2013.01); *A61K 8/0241* (2013.01); *A61K 8/25* (2013.01); *A61K 8/362* (2013.01); *A61K 8/368* (2013.01); *A61K 8/922* (2013.01); *A61K 2800/28* (2013.01); *A61K 2800/43* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 6,106,815 | A | 8/2000 | Kang et al. |
| 6,294,509 | B1 | 9/2001 | Meiwa et al. |
| 6,426,135 | B1 | 7/2002 | Kotani et al. |
| 6,699,963 | B2 | 3/2004 | Noda et al. |
| 7,943,561 | B1 | 5/2011 | Myers et al. |
| 8,008,242 | B1 | 8/2011 | Imam et al. |
| 8,084,409 | B2 | 12/2011 | Lucka et al. |
| 8,084,809 | B2 | 12/2011 | Maeda et al. |
| 8,236,332 | B2 | 8/2012 | Hedges |
| 8,329,628 | B2 | 12/2012 | Cervino |
| 8,470,759 | B2 | 6/2013 | Gonzales et al. |
| 8,546,316 | B2 | 10/2013 | Perez-Prat Vinuesa et al. |
| 8,546,318 | B2 | 10/2013 | D'Ambrogio et al. |
| 8,613,956 | B2 | 12/2013 | Kleiman et al. |
| 8,648,024 | B2 | 2/2014 | Palla-Venkata et al. |
| 8,680,036 | B2 | 3/2014 | Gonzales et al. |
| 2004/0057921 | A1 | 3/2004 | Walsh |
| 2004/0266645 | A1 | 12/2004 | Albrecht et al. |
| 2006/0079421 | A1* | 4/2006 | Wagner ................ A61K 8/0237 510/130 |
| 2008/0226580 | A1 | 9/2008 | Maeda et al. |
| 2009/0054286 | A1 | 2/2009 | Schmit et al. |
| 2009/0318554 | A1 | 12/2009 | Kleiman et al. |
| 2010/0166844 | A1 | 7/2010 | Mougin et al. |
| 2010/0279909 | A1 | 11/2010 | Boyke et al. |
| 2011/0150951 | A1 | 6/2011 | Gonzales et al. |
| 2011/0206748 | A1* | 8/2011 | Cassin .................. A61Q 19/02 424/401 |
| 2011/0262371 | A1 | 10/2011 | Deleersnyder et al. |
| 2011/0287105 | A1 | 11/2011 | Gittleman |
| 2012/0009235 | A1 | 1/2012 | Thilker et al. |
| 2012/0009285 | A1 | 1/2012 | Wei et al. |
| 2012/0071380 | A1 | 3/2012 | Gonzales et al. |
| 2012/0077880 | A1 | 3/2012 | Quan et al. |
| 2012/0077881 | A1 | 3/2012 | Quan et al. |
| 2012/0145172 | A1 | 6/2012 | Shao et al. |
| 2012/0178858 | A1 | 7/2012 | Wnuk et al. |
| 2012/0317736 | A1 | 12/2012 | Gonzales et al. |
| 2012/0321567 | A1 | 12/2012 | Gonzales et al. |
| 2012/0321568 | A1 | 12/2012 | Gonzales et al. |
| 2012/0322713 | A1 | 12/2012 | Perez-Prat Vinuesa et al. |
| 2013/0039961 | A1* | 2/2013 | Gonzales ............. A61K 8/8117 424/401 |
| 2013/0149273 | A1 | 6/2013 | Wei et al. |
| 2013/0317736 | A1 | 11/2013 | Fernandes et al. |

(Continued)

FOREIGN PATENT DOCUMENTS

| | | |
|---|---|---|
| EP | 0490103 | 6/1992 |
| EP | 0670712 | 1/1993 |

(Continued)

OTHER PUBLICATIONS

All Office Actions, U.S. Appl. No. 14/824,357.
U.S. Appl. No. 14/824,357, filed Aug. 12, 2015, Susan Adair Griffiths-Brophy et al.
Exfoliating Facial Scrub with Biodegradable Ecobeads, International Flora Technologies, Inc., Feb. 2016, 6 pages.
International Search Report dated Dec. 1, 2017, Application No. PCT/US2017/054869, 15 pages.
International Search Report and Written Opinion of the International Searching Authority, PCT/US2016/045695, dated Sep. 15, 2016, 11 pages.

*Primary Examiner* — Necholus Ogden, Jr.
(74) *Attorney, Agent, or Firm* — John G. Powell

(57) ABSTRACT

A skin cleansing composition has from about 0.05% to about 15%, by weight of the composition, of a plurality of color stable abrasive particles comprising a non-oxide colorant; and an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof. The abrasive particles are sustainable. The skin cleansing composition has a pH of <6 or from about 4 to about 6.

24 Claims, No Drawings

(56) References Cited

U.S. PATENT DOCUMENTS

| | | |
|---|---|---|
| 2014/0026916 A1 | 1/2014 | Havens et al. |
| 2014/0128306 A1 | 5/2014 | Miyata et al. |
| 2014/0352722 A1 | 5/2014 | Gonzales |
| 2014/0294965 A1 | 10/2014 | Brown et al. |
| 2014/0352723 A1 | 12/2014 | Cermenati et al. |
| 2015/0231042 A1 | 8/2015 | Gonzales et al. |

FOREIGN PATENT DOCUMENTS

| | | |
|---|---|---|
| EP | 1161937 | 12/2001 |
| EP | 2 338 962 A1 | 6/2011 |
| EP | 2 338 963 A1 | 6/2011 |
| EP | 2 338 964 A2 | 6/2011 |
| EP | 2 338 965 A1 | 6/2011 |
| EP | 2 338 966 A1 | 6/2011 |
| EP | 2 431 452 A1 | 3/2012 |
| EP | 2 431 453 A1 | 3/2012 |
| EP | 2 431 454 A1 | 3/2012 |
| EP | 2 431 455 A1 | 3/2012 |
| EP | 2 631 286 A1 | 8/2013 |
| EP | 2 719 752 A1 | 4/2014 |
| EP | 2 808 379 A1 | 12/2014 |
| EP | 2 821 469 A1 | 1/2015 |
| EP | 2 821 472 A1 | 1/2015 |
| EP | 2 847 311 B1 | 4/2016 |
| FR | 2 964 663 A1 | 3/2012 |
| JP | 2004-26788 A | 1/2004 |
| JP | 2007-197602 A | 8/2007 |
| JP | 2000-26229 A | 1/2009 |
| JP | 4331294 B2 | 9/2009 |
| JP | 2010-270085 A | 12/2010 |
| JP | 2012-233057 A | 11/2012 |
| JP | 2012-233128 A | 11/2012 |
| JP | 2013-136732 A | 7/2013 |
| KR | 2009-0056295 A | 6/2009 |
| WO | 2004/043329 A2 | 5/2004 |
| WO | WO2008109270 A1 | 9/2008 |
| WO | 2010/103215 A1 | 9/2010 |
| WO | 2011/079160 A2 | 6/2011 |
| WO | 2011/116963 A2 | 9/2011 |
| WO | 2011/128308 A1 | 10/2011 |
| WO | 2011/133438 A1 | 10/2011 |
| WO | 2011/133508 A1 | 10/2011 |
| WO | 2011/154508 A1 | 12/2011 |
| WO | 2012/167903 A2 | 12/2012 |
| WO | 2012/169518 A1 | 12/2012 |
| WO | 2012/177615 A1 | 12/2012 |
| WO | 2012/177617 A1 | 12/2012 |
| WO | 2012/177628 A1 | 12/2012 |
| WO | 2012/177676 A1 | 12/2012 |
| WO | 2012/177757 A2 | 12/2012 |
| WO | 2013/086251 A1 | 6/2013 |
| WO | 2013/170002 A1 | 11/2013 |
| WO | 2013/187917 A1 | 12/2013 |
| WO | 2013/187918 A1 | 12/2013 |
| WO | 2013/188626 A2 | 12/2013 |
| WO | 2014/174007 A2 | 10/2014 |
| WO | 2014/193913 A1 | 12/2014 |
| WO | 2014/193920 A1 | 12/2014 |
| WO | 2015/132040 A1 | 9/2015 |
| WO | 2015/132041 A1 | 9/2015 |
| WO | 2016/004159 A1 | 1/2016 |
| WO | 2016/004160 A1 | 1/2016 |

\* cited by examiner

SKIN CLEANSING COMPOSITIONS COMPRISING COLOR STABLE ABRASIVE PARTICLES

FIELD OF THE INVENTION

The present invention relates to a skin cleansing composition comprising color stable abrasive particles, and methods of making and using the same.

BACKGROUND OF THE INVENTION

Skin cleansing compositions routinely include abrasive particles for a variety of reasons such as cleansing the skin (e.g., removal of dirt, sebum, or oil) or improving the appearance of the skin (e.g., exfoliation).

Such abrasive particles often comprise a coloring agent of contrasting color to the composition, so that they are more visible to the consumer. A problem impacting colored abrasive particles is the potential bleeding or migration of color from the abrasive particle into the rest of the cleansing composition. Thus particle color stability has been a criterion for particle selection. Not only do particles need to maintain their physical integrity within the body wash or bar formulation so that they can perform their cleaning or exfoliation function, colored particles must also maintain their color. Particles may be acceptable if they maintain both particle integrity and color stability over time.

Colored abrasive particles currently used in skin cleansing compositions are sometimes stabilized by including a non-biodegradable plastic polymer coating around the colored particles in order to bind the color onto the particle and keep it from bleeding, migrating, degrading, or oxidizing. Over the past decade, public concern has been growing on the possible persistence of non-biodegradable, plastic materials that may accumulate in the environment from wash-off personal care products.

Therefore, there is a need for skin cleansing compositions comprising color stable abrasive particles made from sustainable materials that are stabilized by a means other than providing a plastic coating around the particle. Such colored, non-coated particles are more vulnerable to destabilize due to their increased exposure to the many components of the skin cleansing compositions. In addition some alternative approaches such as the use of certain antioxidant materials to stabilize colored abrasive particles are not all efficacious.

Skin cleansing compositions are thus provided herein, with cleansing and exfoliating benefits when applied on skin surfaces, comprising color stable abrasive particles. The abrasive particles comprise non-oxide colorants and have acceptable particle surface safety profile on skin. The composition also comprises select antioxidants and a specific pH range to optimize stability of the colored abrasive particles.

SUMMARY OF THE INVENTION

In an aspect a skin cleansing composition is provided comprising:
a. from about 5% to about 20% by weight of the composition, of a surfactant selected from the group consisting of anionic, cationic, nonionic, amphoteric, zwitterionic, and combinations thereof;
b. from about 0.05% to about 15%, preferably about 0.05% to about 5%, more preferably from about 0.1% to about 0.5%, by weight of the composition of a plurality of abrasive particles comprising:
  i. a mean particle size as expressed by the area-equivalent diameter from about 40 μm to about 5000 μm, preferably from about 600 μm to about 1500 μm, more preferably from about 850 μm to about 1400 μm according to ISO 9276-6:2008; and
  ii. a non-oxide colorant, preferably from about 0.05% to about 3%, more preferably from about 0.1% to about 1% by weight of the abrasive particle;
c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and wherein the skin cleansing composition comprises a pH from 4 to 6, preferably 5 to 6.

In another aspect a method of stabilizing colored abrasive particles in a skin cleansing composition, is provided, the method comprising:
1. making a skin cleansing composition comprising:
  a. from about 5% to about 20% by weight of the composition, of a surfactant selected from the group consisting of anionic, cationic, nonionic, amphoteric, zwitterionic, and combinations thereof;
  b. from about 0.05% to about 15%, preferably about 0.05% to about 5%, more preferably from about 0.1% to about 0.5%, by weight of the composition of a plurality of abrasive particles comprising:
    i. a mean particle size as expressed by the area-equivalent diameter from about 40 μm to about 5000 μm, preferably from about 600 μm to about 1500 μm, more preferably from about 850 μm to about 1400 μm according to ISO 9276-6:2008; and
    ii. a non-oxide colorant, preferably from about 0.05% to about 3%, more preferably from about 0.1% to about 1% by weight of the abrasive particle;
  c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
  wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and
2. adjusting the pH of the composition to a range of pH<6, preferably from 4 to 6, more preferably from 5 to 6.

The composition may also comprise a dermatologically acceptable carrier.

In another aspect, the present invention relates to a method for cleansing a human's skin surface comprising topically contacting the skin surface with a skin cleansing composition according to the present invention, and additionally followed by a rinsing step. It is an advantage of the compositions according to the present invention that they may be used to clean skin surfaces, while providing a good surface safety profile. A further advantage of the present invention is that in the compositions herein, the abrasive particles can be used at very low levels, while still providing the above benefits.

In another aspect, the present invention relates to use of abrasive particles in a skin cleansing composition of the present invention, for delivering a benefit selected from the group consisting of mild skin exfoliation, dirt removal from a skin surface, and combinations thereof.

DETAILED DESCRIPTION OF THE INVENTION

Except as otherwise noted, the articles "a", "an", and "the" mean "one or more."

The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain abrasive particles, and one or more additional or optional ingredients as described hereinafter.

All percentages and ratios used herein are by weight of the total composition. All numeric ranges are inclusive of narrower ranges; delineated upper and lower range limits are interchangeable to create further ranges not explicitly delineated. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

As used herein, "effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein "derivatives" means an ester, ether, amide, hydroxyl, and/or salt structural analogue of the relevant compound.

As used herein "dermatologically acceptable" means that the compositions or components described are suitable for use in contact with human skin tissue, preferably facial or body skin surfaces, without undue toxicity, incompatibility, instability, allergic response, discomfort, and the like.

As used herein "exfoliation" or "mild skin exfoliation" means removal of dead skin cells from the outermost layer of the skin whilst minimizing the risk of over-exfoliating the skin, which may otherwise result in damaged and/or redness to the skin, or discomfort to the user.

As used herein "circularity" means the quantitative, two-dimensional image analysis shape description. A perfectly round particle would have a circularity of 1.00.

As used herein "surface safety profile" means that the compositions or components thereof are not overly abrasive to human skin tissue, particularly human facial skin tissue, so as to not scratch or damage the surface (e.g., redness) while still providing a good cleaning performance on the skin surface.

The term "anhydrous" as used herein, unless otherwise specified, refers to those compositions or materials containing less than about 10%, more preferably less than about 5%, even more preferably less than about 3%, even more preferably zero percent, by weight of water.

The term "multiphase" as used herein means that compositions comprise at least two phases which are chemically distinct (e.g. a surfactant phase and a benefit phase). Such phases are in direct physical contact with one another and are not separated by a barrier. In one aspect of the invention, the composition can be a multiphase composition where the phases of the composition are blended or mixed to a significant degree. In another aspect of the invention, the composition can be a multiphase composition where the phases of the composition are made to occupy separate but distinct physical spaces inside the package in which they are stored, but are in direct contact with one another (i.e., they are not separated by a barrier and they are not emulsified or mixed to any significant degree).

The term "skin cleansing composition" as used herein, refers to compositions intended for topical application to the skin or hair. The compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids. The composition of the present invention is typically extrudable or dispensible from a package.

The compositions of the present invention can be in the form of liquid, semi-liquid, cream, lotion or gel compositions intended for topical application to skin. Examples of skin cleansing compositions of the present invention can include but are not limited to shampoo, conditioning shampoo, body wash, moisturizing body wash, shower gels, skin cleansers, facial skin cleansers, cleansing milks, hair and body wash, in shower body moisturizer, pet shampoo, shaving preparations and cleansing compositions that may be used in conjunction with a disposable cleansing cloth and bar soap.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

As used herein a "non-oxide colorant" means a material that is a dye, pigment, or colorant compound which does not have as its only functionality a metal oxide bond and that may be added to the abrasive particle to provide color. On the other hand an "oxide colorant" means a material that is a dye, pigment, or colorant compound, that may be added to the abrasive particle to provide color, that has as its only functionality a metal oxide bond, for example titanium dioxide, iron (II) oxide, iron (III) oxide, iron (II, III) oxide, zinc oxide, magnesium oxide, aluminum oxide, aluminum hydroxide, boron oxide, green chromium oxide, chromium oxide, copper oxide, manganese oxide, nickel oxide, silver oxide, stannous oxide (tin (II) oxide), stannic oxide (tin (IV) oxide), vanadium oxide, cobalt oxide, silica, bismuth oxide, strontium oxide, barium oxide, tungsten oxide, auric oxide (gold oxide), and mixtures thereof such as mica, etc. In an aspect the composition may be essentially free of oxide colorants.

Abrasive Particles

In an aspect, the abrasive particles have an acceptable surface safety profile and thus are not overly abrasive on contact with skin. In another aspect, the abrasive particles are dermatologically acceptable.

The abrasive particles are selected from the group consisting of: natural waxes, ester waxes, naturally-derived waxes, mineral waxes, oxides, mixed oxides, minerals, clays, carbonates, polysaccharides, sugars, starches, natural polymers, natural fibers, and mixtures thereof.

In an aspect natural waxes include beeswax, *Euphorbia Cerifera* (candelilla) wax, *Copernicia Cerifera* (Carnauba) wax, jojoba esters, jojoba wax, rice bran wax, hydrogenated *camelina sativa* seed oil, castor wax, hydrogenated castor oil, corn wax, bayberry wax, soy wax, or mixtures thereof, e.g. Ecobeads or Ecopearls from Floratech.

Ester waxes/naturally-derived waxes include stearyl stearate, cetyl palmitate, palmityl palmitate, stearyl palmitate, palmityl stearate, cetyl stearate, behenyl behenate, stearyl behenate, behenyl stearate, palmityl behenate, and behenyl palmitate, and combinations thereof.

Mineral waxes include microcrystalline wax, e.g. Metapearls or Parabeads from Floratech, montan wax, ceresin wax, and combinations thereof.

Oxides include silica, silica gel, fumed silica, pyrogenic silica, aerogels, precipitated silica, iron (III) oxide, iron (II) oxide, iron (II, III) oxide, titanium dioxide, alumina, quartz, zinc oxide, magnesium oxide, calcium oxide, and combinations thereof.

Mixed oxides include alumina-silicates, zeolites, silicates, sodium silicate, calcium silicate, e.g. Silicalets from Chongqing Pellets, and combinations thereof.

Minerals include talc, pumice, perlite, vermiculite, mica, and combinations thereof.

Clays include bentonite, montmorillonite, kaolin, and combinations thereof.

Carbonates include sodium carbonate, sodium hydrogen carbonate, calcium carbonate, potassium carbonate, potassium hydrogen carbonate, magnesium carbonate, zinc carbonate, and combinations thereof.

Natural fibers include wood, cotton, flax, hemp, lignin, and combinations thereof.

Polysaccharides/sugars/starch include cellulose, mannitol, lactose, or mixtures thereof, e.g. Unispheres from Induchem, methyl cellulose, ethyl cellulose, propyl cellulose, hydroxypropyl cellulose, hydroxylpropyl methylcellulose, e.g. Methocel from Dow Chemical, hydroxyethyl cellulose, and combinations thereof.

Natural polymers, include carrageenan, alginate, argose, agar, glucomannan, gellan, pectin, and combinations thereof.

In an aspect the abrasive particles are essentially free of polyethylene. In another aspect the abrasive particles are essentially free of polymer/copolymer particles wherein the polymer/copolymers are selected from the group consisting of polyethylene, polypropylene, polystyrene, polyethylene terephthalate, polyester, polyurethanes, polyamides, polycarbonate, polyvinyl chloride, polyvinyl acetate, polymethyl methacrylate and copolymers, polyhydroxy alkanoate (PHA) (such as poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof), and mixtures thereof.

In certain aspects, the abrasive particles of the present invention are generally spherical, ellipsoidal, amorphous shaped, or drop-shaped. In another aspect the abrasive particles herein do not have sharp edges or tips, do not have edges or surfaces having concave curvature such as those described in U.S. Pat. No. 8,546,316, Perez-Prat Vinuesa et al, issued Oct. 1, 2013 and/or U.S. Pat. No. 8,680,036, Gonzales et al, issued Mar. 25, 2014.

Circularity is a quantitative, 2-dimension image analysis shape description as measured according to ISO 9276-6: 2008(E) section 8.2 as implemented via the Occhio Nano 500 Particle Characterisation Instrument with its accompanying software Callistro version 25 (Occhio s.a. Liege, Belgium). Circularity is a preferred mesoshape descriptor and is widely available in shape analysis instrument such as in Occhio Nano 500 or in Malvern Morphologi G3. Circularity is sometimes described in literature as being the difference between a particle's shape and a perfect sphere.

A circularity of 1 describes a perfectly spherical particles or disc particle as measured in a two dimensional image. Circularity is calculated by the following equation:

$$C = \sqrt{\frac{4\pi A}{P^2}}$$

wherein A is projection area, which is a 2D descriptor, and P is the perimeter length of the particle.

In one aspect, the particles herein have a mean circularity of greater than 0.90, or from 0.90 to 1.00, or from 0.95 to 1.00, or nearly about 1.00. The particles are mainly spherical. Mean data are extracted from volume-based vs. number-based measurements. By the term "mean circularity", it is meant the average of the circularity values of each particle (excluding particles having an ECD of below 10 microns)

taken from a population of at least about 10,000 particles; however greater sampling sizes are envisioned such as above about 50,000 particles or about 100,000 particles.

Abrasive particles according to the present invention, when formulated into the skin cleansing compositions, provide good cleaning/cleansing performance on human skin surfaces, while providing a good surface safety profile. In particular, a benefit is delivered and is selected from the group consisting of mild skin exfoliation, good dirt removal from a skin surface, and combinations thereof, preferably without damaging the skin surface or causing discomfort to the users to provide a acceptable surface safety profile.

In another aspect the abrasive particles may be selected from those disclosed in US Patent Publication 2014/0294965, published on Oct. 2, 2014, Brown et al., International Flora Technologies, also called Floratech. Thus in an aspect the abrasive particles may comprise a derivative, of a botanically-sourced emollient, stearyl stearate, and at least one of: candelilla wax, rice bran wax, sunflower wax, jojoba esters, carnauba wax, bees wax, corn wax, a saturated wax-ester, castor wax, ouricury wax, hydrogenated lanolin, and a hydrogenated triglyceride wax. The botanically-sourced emollient may compose botanical lipid materials. For example, in some aspects, the botanical lipid materials of the botanically-sourced emollient may comprise fatty acids, esters of fatty acids, fatty alcohols, esters of fatty alcohols, esters of fatty alcohols with fatty acids, sugar alcohols, isopropyl esters, wax esters and/or combinations thereof extracted from the seed oil of the jojoba plant (*Simmondsia chinensis*). In one aspect; the botanically sourced emollient may comprise jojoba esters. In some aspects, the exfoliating particles may comprise about 1% to about 3%, by weight of the particles, of jojoba esters. In other aspects the abrasive particles comprise about 1% to about 3% of a botanically-sourced emollient, about 90% to about 95% of stearyl stearate wax; and about 4% to about 7% of candelilla wax, by weight of the abrasive particle, wherein the botanically-sourced emollient comprises a jojoba ester. The material may be supplied by Floratech under their Ecobeads and Ecopearls tradenames.

In an aspect the composition comprises from about 0.05% to about 15%, preferably about 0.05% to about 5%, more preferably from about 0.1% to about 2%, or about 0.1% to about 0.5%, by weight of the composition of the abrasive particles.

Hardness

The abrasive particles should be hard enough to provide good cleaning/cleansing performance while providing good surface safety and/or skin feel acceptability. The abrasive particles in the present invention may have Shore® D hardness from about 35, 40, 45, or 50 durometer to about 60, 65, or 75 durometer as determined according to ASTM D2240-05 (2010). Shore® D hardness measurement is carried out by using an ASTM durometer, such as the Type D Style Durometer available from Pacific Transducer Corp. of Los Angeles, Calif., or from ELECTROMATIC Equipment Co., Inc. 600 Oakland Ave Cedarhurst, N.Y. 11516 (description of the stylus digital or gauge instrument at http://www.checkline.com/durometers).

Mean Particle Size

Good skin cleansing efficiency can be achieved with the abrasive particles having a certain mean particle size as defined by their area-equivalent diameter (ISO 9276:2008 (E) section 6) also called Equivalent Circle Diameter (ECD) (ASTM F1877-05 Section 11.3.2). Mean ECD of particle population is calculated as the average of respective ECD of each particle of a particle population of at least 1,000 preferably above 10,000 particles, preferably above 50,000 particles, more preferably above 100,000 particles after excluding from the measurement and calculation the data of particles having area-equivalent diameter (ECD) of below 10 micrometers. Mean data are extracted from volume-based vs. number-based measurements. In an aspect, abrasive particles have a mean particle size as expressed by the area-equivalent diameter of from about 40 μm, 500 μm, 650 μm, or 850 μm to about 1,000 μm, 1,200 μm, 1,500 μm, 2,000 μm, 5,000 μm or preferably from about 850 μm to about 2,000 μm.

Typical shearing or graining methods may be used to reduce the above material into abrasive particles. Thereafter, grain shaping methods described in the art may be employed such as agglomerating, printing, carving, etc. As examples, suitable ways of reducing the abrasive material into abrasive cleaning particles herein is to grind or mill the material using jaw Crushers mills or rotor mills or cutting or blade or knife mills, or impact or rotor or disc mills such as manufactured by Retschz (see http://www.retsch.com/products/milling). In another aspect the abrasive particles are reduced into particles by grinding or milling, coacervation, extrusion, spheronization, etc. If needed the temperature needs to be kept constant during the grinding operation, whereas suitable grinding temperature in some aspects should not exceed 60° C. In some cases, the optimal grinding temperature needs to be below 30° C., sometimes below 0° C. and in some cases grinding is better achieved in cryogenic condition using refrigerant media such as $CO_2$ or nitrogen in liquid conditions.

Other suitable means include the use of eroding tools such as a high speed eroding wheel with dust collector wherein the surface of the wheel is engraved with a pattern or is coated with abrasive sandpaper or the like to promote formation of the abrasive cleaning particles herein.

Alternatively the abrasive raw material can be broken into pieces of a few centimeter dimensions by manually chopping or cutting, or using a mechanical tool such as a lumpbreaker, for example the Model 2036 from S Howes, Inc. of Silver Creek, N.Y.

Preferably, the abrasive cleaning particles obtained via grinding or milling operation are single particles.

Shaping processes are sometimes facilitated by mixing previous abrasive materials as fillers within a thermoplastic or solidifying matrix. Such processes e.g.: including selection of matrix and respective load of filler are well known in art.

Colorants and Antioxidants

In one aspect the plurality of abrasive particles further comprises a colorant, to provide colored abrasive particles. The abrasive particles used in the present invention may be colored by the use of suitable dyes and pigments, which may be selected from the group consisting of organic pigments, inorganic pigments, interference pigments, lakes, natural colorants, pearlescent agents, dyes, and mixtures thereof. In an aspect the pigments, lakes and/or dyes are hydrophobic. Other dyes and pigments are disclosed in *International Cosmetic Ingredient Dictionary and Handbook*, $10^{th}$ Edition, Volume 3, 2004, Colorants, pp. 2194-2197. Other useful colorants may be selected from those listed in US 2012/0071380 Gonzales et al., published on Mar. 22, 2012.

In an aspect the abrasive particles comprise a safe and effective amount of a colorant, and/or from about 0.001% to about 5% by weight of the abrasive particles, of a colorant; in another aspect from about 0.05% to about 3%, in another aspect from about 0.1% to about 1% by weight of the abrasive particles, of a colorant.

In an aspect the colorant may be a non-oxide colorant that comprises or is selected from the group consisting of ultramarine blue, ferric ammonium ferrocyanide, ferric ferrocyanide, Blue No. 1 Lake, copper phthalocyanine (blue No. 15), yellow lakes #3, yellow lake #5, yellow lake #6, red lakes, red dyes such as red dye #4, red dye #30, red dye #40, green #6, violet #2 and combinations thereof.

In another aspect the non-oxide colorant is selected from the group consisting of ultramarine blue, ferric ammonium ferrocyanide, ferric ferrocyanide, Blue No. 1 Lake, copper phthalocyanine (blue No. 15) and combinations thereof.

A problem impacting colored abrasive particles, especially non-oxide colorants, is the bleeding or migration of color from the abrasive particles into the rest of the cleansing composition. This can be more problematic if the colored abrasive particles are used at higher concentrations or are used in opaque or white compositions or are used in higher/basic pH compositions.

Thus, in an aspect the colored abrasive particles are "color stable". As used herein "color stable" means that the colorant will not significantly bleed or migrate into the cleansing composition for the intended use and storage period.

In an aspect the colorant is added to the abrasive particle material as a blend and then mixed in order to achieve a homogeneous mixture. Other coloring processes for the abrasive particle are disclosed in US 2012/0071380, Gonzales et al., published on Mar. 22, 2012.

In an aspect the skin care composition comprises an antioxidant, which may stabilize the colored abrasive particles. The antioxidant may be selected from the group consisting of tocopherol acetate (Vitamin E Acetate), butylated hydroxyanisole (BHA), butylated hydroxytoluene (BHT), sodium benzotriazolyl butylphenol sulfate (Tinogard HS from BASF), Vitamin C (ascorbic acid) and combinations thereof.

The antioxidant is used at a level of from about 0.05% to about 5%, preferably from about 0.10% to about 1% by weight of the skin care composition.

Skin Cleansing Compositions

The present invention is directed to a skin cleansing composition comprising abrasive particles present at a level of from about 0.05 wt % to about 15 wt %, preferably from about 0.05 wt % to about 5 wt %, more preferably from about 0.1 wt % to about 0.5 wt %, and a dermatologically acceptable carrier.

The skin cleansing compositions according to the present invention are designed as skin cleansers for a variety of human skin surfaces. Examples of the skin cleansing compositions include, a facial cleanser, a body wash, a hand cleanser, a bar soap, or a body cleanser. In a preferred aspect, the skin cleansing compositions herein are suitable for use as a body wash.

In another aspect, the skin cleansing compositions have a viscosity in the range of from about 100 cps to about 1,000,000 cps, preferably from about 1,000 to about 300,000 cps, or more preferably from about 5,000 to about 200,000 cps. The viscosity is measured at 20 sec$^{-1}$ and 20° C. with a Rheometer, model AR 1000 (Supplied by TA Instruments) with a 4 cm conic spindle in stainless steel, 2° angle (linear increment from 0.1 to 100 sec$^{-1}$ in max. 8 minutes).

pH

In another aspect, the skin cleansing compositions herein are neutral compositions. In other preferred aspects, the skin cleansing compositions herein have a pH in the range of from about 4.0 to about 6.0, more preferably from about 5.5 to about 6.0, more preferably pH<6, wherein the pH is measured at 25° C. Composition pH also plays a role in the stability of colored abrasive particles and some colorants, such as non-oxide colorants, are less stable in the composition at non-neutral pH range.

Accordingly, the skin cleansing compositions herein may comprise suitable bases and acids to adjust the pH. A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (e.g., monoethanolamine), urea and urea derivatives, polyamine, etc. Typical levels of such bases, when present, are from about 0.01 wt % to about 5.0 wt %, preferably from about 0.05 wt % to about 3.0 wt %, and more preferably from about 0.1 wt % to about 0.6 wt %, wherein the wt % is relative to the total weight of the composition.

The skin cleansing compositions herein may comprise an acid to trim its pH to the required level. Despite the presence of an acid, if any, the skin cleansing compositions herein will maintain their preferred neutral, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and mixtures thereof. A mixture of the acids may be commercially available from BASF under the trade name Sokalan® DCS. A suitable inorganic acid is selected from the group consisting hydrochloric acid, sulfuric acid, phosphoric acid and mixtures thereof. A typical level of such an acid, when present, is from about 0.01 wt % to about 5.0 wt %, preferably from about 0.04 wt % to about 3.0 wt % and more preferably from about 0.05 wt % to about 1.5 wt %, wherein the wt % is relative to the total weight of the composition.

Cleansing/Surfactant Phase

One of the phases of the skin cleansing composition of the present invention is a cleansing phase, which is a surfactant phase. The surfactant phase may comprise linear, sulfate surfactants. Examples of such surfactants include sodium lauryl sulfate or ammonium lauryl sulfate in which these materials do not contain any ethoxylation or propoxylation. Additional surfactants include sodium laureth sulfate or ammonium laureth sulfate in which the materials contain one or more ethoxylation and/or propoxylation. Examples of such surfactants include sodium laureth-1 sulfate, sodium laureth-2 sulfate, sodium laureth-3 sulfate, ammonium laureth-1 sulfate, ammonium laureth-2 sulfate, or ammonium laureth-3 sulfate. Such materials can be described as SLEnS or ALEnS in which n is the average number of moles of ethoxylation and/or propoxylation.

One of the phases of the skin cleansing composition of the present invention is a cleansing phase, which is a surfactant phase. The surfactant phase may comprise a structured domain that comprises a surfactant and optionally a cosurfactant. The structured domain may be an opaque structured domain, which is preferably a lamellar phase. The lamellar phase can provide resistance to shear, adequate yield strength to suspend particles and droplets and at the same time provides long term stability, since it is thermodynamically stable. The lamellar phase tends to have a viscosity that minimizes the need for viscosity modifiers.

The term "structured" or "structuring" as used herein means having a rheology that confers stability on the composition. The degree of structure is determined by characteristics for example may be determined by the Yield Stress, as determined by the Yield Stress Method disclosed in U.S. Ser. No. 15/091,682, filed Apr. 6, 2016, (P&G Case 14301) in the section "Test Methods". Accordingly, in an aspect a surfactant phase of the composition of the present invention is considered "structured," if the surfactant phase has of at least about 0.1 Pa.

Examples of some suitable branched surfactants include anionic surfactants such as the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium, and sodium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al. on Jan. 1, 2002. Suitable examples of alcohols are Safol™ 23 and Neodol™ 23. Suitable examples of alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

The surfactant may also be STnS, wherein n can define average moles of ethoxylation. A structured cleansing phase can include from about 5% to about 20%, from about 7% to about 18%, from about 5% to about 10%, from about 9% to about 16%, from about 11% to about 14%, by weight of the composition, of STnS, wherein n can range from about 0 to about 3, from about 0.5 to about 3, from about 1.1 to about 3. Such described benefits of STnS are disclosed in U.S. patent application Ser. No. 13/157,665.

A material such as ST2S or ST3S, for example, may comprise a significant amount of molecules which have no ethoxylate, 1 mole ethoxylate, 2 mole ethoxylate, and so on in a distribution which can be broad, narrow or truncated, still comprising ST2S wherein the average of the distribution is about 2 or ST3S wherein the average of the distribution is about 3.

STnS is optionally combined with SLS in order to form a surfactant system. In one aspect, the skin cleansing compositions of the present invention comprise less than about 5% SLS, alternatively less than about 4% SLS, alternatively less than about 3% SLS, alternatively less than about 2% SLS, alternatively less than about 1% SLS, alternatively between about 0.1% SLS and about 2% SLS, alternatively about 0% SLS. Without wishing to be bound by theory, it is believed that the presence of SLS increases the harshness of the composition, negating at least in part the mildness benefits and/or the efficacy of the benefit agents within the skin cleansing composition.

Further, the surfactant phase can comprise a structuring system wherein the structuring system can comprise an associative polymer, a non-associative polymer, an electrolyte, trihydroxystearin, and combinations thereof. The structuring system can comprise from about 0.05% to about 5%, from about 0.05% to about 1%, from about 0.07% to about 0.5%, or from about 0.1% to about 0.3%, by weight of the composition, of a structuring material such as a non-associative polymer. The structuring system can comprise from about 0.001% to about 5%, from about 0.005% to about 0.5%, from about 0.007% to about 0.05%, from about 0.008% to about 0.04%, or from about 0.01% to about 0.03%, by weight of composition, of an associative polymer. As noted herein, stability of a composition can be maintained or enhanced even with the reduction of associative polymer with the addition of a non-associative polymer. In an aspect the composition may comprise from about 0.05% to about 5%, from about 0.05% to about 1% by weight of the composition, of a structuring material selected from the group consisting of an associative polymer, trihydroxystearin or combinations thereof.

Associative polymers can be crosslinked, alkali swellable, associative polymers comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae or micellar, to confer structure to the surfactant phase and keep the associative polymer from collapsing and losing effectiveness in the presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, or other linear, branched, saturated, or unsaturated alkyl or alketh hydrocarbon side chains.

Crosslinked, associative polymers having certain % HM and certain carbon numbers of hydrophobic end groups of alkyl side chains can provide significant enhancement of structure to compositions comprising a structured surfactant, especially to compositions comprising reduced levels of surfactant. Such associative polymers can also provide the above structure at surprisingly low levels of polymer structurant. Concentrations of associative polymers of up to about 5% or even 10% have been known to provide a sufficient amount of structure (e.g., exemplary compositions of U.S. Pat. No. 7,119,059 (Librizzi, et al.) and U.S. Pat. No. 6,897,253 (Schmucker-Castner, et al.). When an associative polymer % HM and an alkyl side chain number of carbons can be optimized, the structure of an aqueous structured surfactant phase can be increased using only less than about 3 wt %, less than about 2%, less than about 1%, and less than about 0.2%, of an associative polymer, as a percentage of an aqueous structured surfactant phase.

The acidic monomer can comprise any acid functional group, for example sulfate, sulfonate, carboxylate, phosphonate, or phosphate or mixtures of acid groups. The acidic monomer can comprise, for example, a carboxylate. Alternatively, the acidic monomer can be an acrylate, including acrylic acid and/or methacrylic acid. The acidic monomer can comprise a polymerizable structure, e.g., vinyl functionality. Mixtures of acidic monomers, for example acrylic acid and methacrylic acid monomer mixtures, may be useful as well.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

Sometimes, the hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the composition comprising a structured surfactant with low levels of polymer structurant.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (palmityl) alkyl hydrophobic side chains with about 0.7% hydrophobic modification, but a percentage hydrophobic modification can be up to an aqueous solubility limit in surfactant compositions (e.g., up to 2%, 5%, or 10%). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

As set forth above, the structured cleansing phase of a composition can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

As set forth above, the structured surfactant phase or surfactant phase may comprise from about 0.05% to about 10% or from about 0.5% to about 5% by weight, of an electrolyte. The electrolyte may comprise an anion selected from the group consisting of phosphate, chloride, sulfate, citrate, and mixtures thereof, and a cation selected from the group consisting of sodium, ammonium, potassium, magnesium, and mixtures thereof. The electrolyte may also be selected from the group consisting of sodium chloride, ammonium chloride, sodium sulfate, ammonium sulfate, and mixtures thereof.

The composition can be optionally free of or substantially free of sodium lauryl sulfate, hereinafter SLS, and/or ammonium lauryl sulfate, hereinafter ALS, and can comprise at least a 70% lamellar structure. However, in an alternative arrangement, the structured cleansing phase can comprise at least one surfactant, wherein the at least one surfactant includes SLS and/or ALS. Suitable examples of SLS are described in U.S. patent application Ser. No. 12/817,786.

Cosurfactant

The skin cleansing compositions of the present invention may further comprise a cosurfactant. Cosurfactants may comprise from about 0.1% to 20%, alternatively from about 1% to about 10% by weight of the composition. Cosurfactants comprise amphoteric surfactants, zwitterionic surfactants, and mixtures thereof. In one aspect, the composition comprises at least one amphoteric surfactant and/or at least one zwitterionic surfactant. Amphoteric surfactants suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. In one aspect, the multiphase composition can comprise an amphoteric surfactant that is selected from the group consisting of sodium lauroamphoacetate, sodium cocoamphoacetate, disodium lauroamphoacetate, disodium cocodiamphoacetate, and mixtures thereof. Moreover, amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase composition include betaines, including cocoamidopropyl betaine and laurylamidopropyl betaine.

Moisturizer

The skin cleansing composition may comprise a dermatologically acceptable moisturizer. Such dermatologically acceptable moisturizer includes lipids of natural or petroleum based sources. Lipids of natural sources include various vegetable oils such as soybean oil, coconut oil, palm oil, palm stearine oil. canola oil, sunflower oil, corn oil. Other such natural lipids contain various plant and extract butters such as shea butter, cocoa butter. Petroleum sources oils contain petrolatum and various mineral oils. Suitable examples of oils for use in the skin cleansing composition herein are found in U.S. 2013/039961 (P&G).

Carrier

The skin cleansing composition may comprise a dermatologically acceptable carrier. Dermatologically acceptable carriers may be selected for various stability, aesthetics, and/or compatibility with other materials present in the skin cleansing composition. Suitable carriers include water and/or water soluble solvents. The skin cleansing composition may comprise from about 1% to about 95% by weight of water and/or water equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, octanediol, ethylhexanediol, decanediol; glycerin; water, and mixtures thereof. In certain aspects, the skin cleansing composition comprises water, diols, glycerin, and combinations thereof.

Suitable carriers also include oils. The skin cleansing composition may comprise from about 1% to about 95% by weight of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. However, certain skin cleansing product forms (i.e., solid or semisolid stick) may require non-fluid oils. The oils may be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm Hg at 25° C. Volatile oils may be used to provide a lighter feel when a heavy, greasy film is undesirable.

Suitable oils include volatile oils. In certain aspects, the volatile oils may have a viscosity ranging from about 0.5 to about 5 centistokes (cst) at 25° C. Volatile oils may be used to promote more rapid drying of the skin care composition after it is applied to skin.

Non-volatile oils are also suitable for use in the composition. Non-volatile oils are often used for emolliency and protective properties. Non-volatile oils preferably may have a viscosity ranging from about 5 cst to about 2,000,000 cst or from about 20 cst to about 200,000 cst. Suitable examples of oils for use in the skin cleansing composition of the present invention are found in U.S. 2013/039961 (P&G).

Optional Skin Cleansing Ingredients

The skin cleansing composition may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, phytosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratin protecting agents, emollients, moisturizers, and combinations thereof.

Method of Using the Skin Cleansing Compositions

The present invention encompasses a method for cleansing a human's skin surface comprising topically contacting the skin surface with a skin cleansing composition according to the present invention. Suitable skin surfaces herein include body, hands, and facial skin surfaces.

In a preferred aspect, the composition according to the present invention is topically applied to the body or facial skin surface. "Facial skin surface" refers to one or more of the forehead, periorbital, cheek, perioral, chin, and nose skin surfaces.

The composition herein may be in its neat form or in its diluted form. By "in its neat form", it is to be understood that the composition is applied directly onto the skin surface to be treated without undergoing any dilution. By "diluted form", it is meant herein that the composition is diluted by the user typically with water. The composition is diluted prior to use to a typical dilution level of up to 10 times its weight of water. As usually recommended dilution level is a 10% dilution of the composition in water.

The composition herein may be applied using the palms of the hands and/or fingers, or using an appropriate implement, such as a puff, loofah, cloth, sponge, mask, razor, wand, cotton ball, swab, or pad, soaked in the diluted or neat composition herein. Furthermore, once applied onto the skin surface the composition may be agitated over the skin surface.

The method herein may optionally contain an additional rinsing step, preferably after the application of the composition. By "rinsing", it is meant herein contacting the surface cleaned/cleansed with the method according to the present invention with substantial quantities of appropriate solvent, typically water, directly after the step of applying the liquid composition herein onto the skin surface. By "substantial quantities", it is meant herein between 0.001 L and 1 L of water per $m^2$ of skin surface, more preferably between 0.1 L and 1 L of water per $m^2$ of skin surface.

Test Methods

Particle Size Distribution Test Method

The particle size ranges of the abrasive particles herein are measured using a HORIBA LA-950 Particle Size Analyzer commercially available from Horiba International Corporation of Irvine, Calif.

The HORIBA LA-950 Particle Size Analyzer is set to operate in manual mode for the particle analyses. The main operational parameter settings are:

| | |
|---|---|
| Refractive index | 1.470-0.000i, (Water 1.333) |
| Circulation Speed | 6 (of 15) |
| Agitation Speed | 3 (of 15) |
| Ultra Sonic Power | 1 (of 7) |
| Ultra Sonic Time | Blank - 1 min, Sample - 3 min |

For each analysis the sample cup is filled with 200 mL of purified water, circulate, agitate and sonicate for one minute to remove bubbles from the system. Next, the laser is aligned and the blank sample is recorded prior to each analysis.

Each sample is prepared by gentle stirring with a spatula for a minute to alleviate any settling or agglomeration of aggregates. While the water in the sample cup is circulating and agitating, add enough sample (3 to 5 mL) using a transfer-tube to reduce the percent transmittance from 100 to 90+/−2%.

Once the baseline signal has stabilized to ensure the 90+/−2% transmittance, the sample is sonicated at power level 1 for 3 minutes before a measurement is taken. This process is repeated four times for each sample and the average of the analysis is reported.

Exemplary Skin Cleansing Compositions

The following compositions were made by mixing the listed ingredients in the listed proportions (weight %) below. Mixing may be done by devices and techniques known in the art. Examples 1-6 of Table 1 and Examples 1-3 of Table 2 herein are meant to exemplify the present invention but are not necessarily used to limit or otherwise define the scope of the present invention.

TABLE 1

Examples of Non-Lipid Based Body Washes

| Ingredient | 1 | 2 | 3 | 4 | 5 | 6 |
|---|---|---|---|---|---|---|
| SLE3S[1] | 6.5 | 6.5 | 6.5 | 6.5 | 6.5 | 6.5 |
| CAPB[2] | 1.0 | 1.0 | 1.0 | 1.0 | 1.0 | 1.0 |
| SLS | 2.5 | 2.5 | 2.5 | 2.5 | 2.5 | 2.5 |
| Trihydroxystearin[3] | 0.5 | 0.5 | 0.5 | 0.5 | 0.5 | 0.5 |
| Sodium Benzoate | 0.2 | 0.2 | 0.2 | 0.2 | 0.2 | 0.2 |
| Methylchloroisothiazolinone/Methylisothiaxolinone[4] | 0.03 | 0.03 | 0.03 | 0.03 | 0.03 | 0.03 |
| Fragrance | 1.0 | 1.0 | 1.0 | 1.25 | 1.25 | 1.25 |
| Disodium EDTA | 0.1 | 0.1 | 0.1 | 0.1 | 0.1 | 0.1 |
| Citric Acid | 0.1 | 0.2 | 0.2 | 0.1 | 0.2 | 0.2 |
| NaCl | 2.0 | 2.0 | 2.0 | 2.0 | 2.0 | 2.0 |
| Abrasive Particle[5] | 0.2 | 0.2 | 0.2 | — | — | — |
| Abrasive Particle[6] | — | — | — | 0.2 | 0.2 | 0.2 |
| Anti-Oxidant[7] | — | — | 0.1 | — | — | 0.1 |
| Water | QS | QS | QS | QS | QS | QS |
| pH | 6.6 | 5.7 | 5.7 | 6.6 | 5.7 | 5.7 |
| Yield Stress (Pa) | 0.5 | 0.5 | 0.5 | 0.5 | 0.5 | 0.5 |
| Color Stability | Good | Poor | Good | Good | Poor | Good |

[1]SLE(n)S where n equals moles of ethoxylation can be obtained from Procter & Gamble, Co., Cincinnati, OH USA.
[2]Cocoamidopropyl Betaine can be obtained from Stepan Corp., Northfield, IL USA.
[3]Thixcin ® is the tradename for trihydroxystearin obtained from Elementis Specialties Co., Windsor, NJ USA.
[4]Kathon CG ™ is the tradename available from Rohm & Haas Company, Philadelphia, PA USA.
[5]Ecobeads Lapis is a tradename available from Floratech, Chandler, AZ, USA. Particle contains ultramarines colorant. Particle size is about 400 to 1,000 microns.
[6]Silica particles from Kobo, Tokyo, Japan. Particle contains ferric ammonium ferrocyanide. Particle size is about 600 to 1500 microns.
[7]BHT

TABLE 2

Examples of Lipid-Based Body Washes

| Ingredient | 1 | 2 | 3 |
|---|---|---|---|
| ST2S[1] | 9.3 | 9.3 | 9.3 |
| CAPB[2] | 2.8 | 2.8 | 2.8 |
| Trideceth-3 (HLB = 8)[3] | 0.5 | 0.5 | 0.5 |
| Sodium Benzoate | 0.2 | 0.2 | 0.2 |
| Methylchloroisothiazolinone/Methylisothiaxolinone[4] | 0.05 | 0.05 | 0.05 |
| Fragrance | 1.0 | 1.0 | 1.0 |
| Disodium EDTA | 0.1 | 0.1 | 0.1 |
| Abrasive Particle[5] | 0.2 | 0.2 | 0.2 |
| Citric Acid | 0.2 | 0.2 | 0.2 |
| NaCl | 4.8 | 4.8 | 4.8 |
| Xanthan Gum[6] | 0.2 | 0.2 | 0.2 |
| N-Hance CG-17[7] | 0.4 | 0.4 | 0.4 |
| Aqupec[8] | 0.05 | 0.05 | 0.05 |
| Anti-Oxidant[9] | — | — | 0.1 |
| Petrolatum | 6.9 | 6.9 | 6.9 |
| Glyceryl Monooleate | 0.1 | 0.1 | 0.1 |
| Water | QS | QS | QS |
| pH | 6.5 | 5.7 | 5.7 |
| Color Stability | Good | Poor | Good |
| Yield Stress (Pa) | 1.0 | 1.0 | 1.0 |

[1]Sodium Trideceth(n) Sulfate where n = 2 moles ethoxylation can be obtained from Stepan Corp., Northfield, IL USA.
[2]Cocoamidopropyl Betaine can be obtained from Stepan Corp., Northfield, IL USA.
[3]Iconal TDA-3 ® is available from BASF Corp., Florham Park, NJ USA.4.
[4]Kathon CG ™ is the tradename available from Rohm & Haas Company, Philadelphia, PA USA.
[5]Ecobeads Lapis is a tradename available from Floratech, Chandler, AZ, USA. Particle contains ultramarines colorant. Particle size is about 400 to 1,000 microns.
[6]Keltrol 1000 ® can be obtained from CP Kelco, Chicago, IL USA.
[7]N-Hance ™ polymer series is commercially available from Aqualon, part of Ashland Specialty Co., Covington, KY USA.
[8]AQUPEC ® SER-300 made by Sumitomo Seika of Tokyo, Japan.
[9]BHT As shown in Table 1, the color stability of the particles of comparative examples 2 & 5 at a low pH (pH<6), is poor. Particle color migration (bleeding) into the product composition is observed rendering the product unacceptable to the consumer. Maintaining the product composition at a high pH (pH>6) may overcome the poor particle color stability as shown in control examples 1 & 4. For a low pH product (pH<6), the colored abrasive particles are also rendered color stable if a select anti-oxidant is added to the product composition. As shown in inventive examples 3 & 6, addition of an anti-oxidant allowed for improved color stability even at a low pH (pH<6) when non-oxide colorants such as ultramarines and ferric ammonium ferrocyanide, are used. Such particle color stability is required for non-oxide colorants as shown in Table 1 with colorants such as ultramarines and ferric ammonium ferrocyanide as non-limiting non-oxide colorants.

As shown in Table 2, the color stability of the particles of comparative example 2, at a low pH (pH<6), is poor. Particle color migration (bleeding) into the product composition is observed rendering the product unacceptable to the consumer. Maintaining the product composition at a high pH (pH>6) may overcome the poor particle color stability as shown in control example 1. For a low pH product (pH<6) the colored abrasive particles are also rendered color stable if a select anti-oxidant is added to the product composition. As shown in inventive example 3, addition of an anti-oxidant allowed for improved color stability even at a low pH (pH<6) when non-oxide colorants such as ultramarines, are used. Such particle color stability is required for non-oxide colorants as shown in Table 2 with colorants such as ultramarines as non-limiting non-oxide colorants.

Color Stability

A series of anti-oxidant materials were tested in a body wash formula. Certain anti-oxidant materials as shown in Table 3 were able to maintain particle color stability when included in a body wash formulation while other anti-oxidant materials did not provide adequate particle color stability.

Particle color stability was ascertained by adding the colored-particle (non-oxide colorants) to the body wash chassis having a pH of about 5.7, and placing at various temperatures above room temperature and monitoring the particle color appearance/integrity over time. Each colored-particle body wash chassis was compared to a control sample. The control sample was a freshly made sample that was used to compare any color instability issues. Products were placed at temperatures from room temperature up to 80° C. and monitored for 1 day up to two years. Colored-particles that showed no color change were determined to be "Good". Samples with little/minor change were determined to be "Acceptable". Samples that had too much change or showed complete color loss were determined to be "Poor". Samples were judged by several observers (typically four individuals).

TABLE 3

Particle Color Stability

| Anti-Oxidant | Water Solubility | 10 Day/50° C. | 2 wks/60° C. |
|---|---|---|---|
| Tocopherol Acetate (Vitamin E Acetate) | Insoluble | Good | Good |
| Butylated Hydroxyanisole (BHA) | Insoluble | Good | Good |
| Butylated Hydroxytoluene (BHT) | Insoluble | Good | Good |
| Sodium Benzotriazolyl Butylphenol Sulfate (Tinogard HS from BASF) | Soluble (also alcohol) | Good | Good |
| Vitamin C (Ascorbic Acid) | Soluble | Acceptable | Acceptable |
| tert-Butylhydroquinone (TBHQ) | Soluble | Poor | Poor |
| Propyl 3,4,5-Trihydroxybenzoate (Propyl Gallate) | Insoluble | Poor | Poor |
| 6-Ethoxy-1,2-Dihydro-2,2,4-Trimethylquinoline (Ethoxyquin) | Insoluble | Poor | Poor |
| Etidronic acid or 1-hydroxyethane 1,1-diphosphonic acid (HEDP) | Soluble | Poor | Poor |

Additional Examples

1. A skin cleansing composition comprising:
a. from about 5% to about 20% by weight of the composition, of a surfactant selected from the group consisting of anionic, cationic, nonionic, amphoteric, zwitterionic, and combinations thereof;
b. from about 0.05% to about 15%, preferably about 0.05% to about 5%, more preferably from about 0.1% to about 0.5%, by weight of the composition of a plurality of abrasive particles comprising:
  i. a mean particle size as expressed by the area-equivalent diameter from about 40 μm to about 5000 preferably from about 600 μm to about 1500 more preferably from about 850 μm to about 1400 μm according to ISO 9276-6:2008; and
  ii. a non-oxide colorant, preferably from about 0.05% to about 3%, more preferably from about 0.1% to about 1% by weight of the abrasive particle;
c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and
wherein the skin cleansing composition comprises a pH from 4 to 6, preferably 5 to 6.

2. A method of stabilizing colored abrasive particles in a skin cleansing composition, the method comprising:
  1. making a skin cleansing composition comprising:
    a. from about 5% to about 20% by weight of the composition, of a surfactant selected from the group consisting of anionic, cationic, nonionic, amphoteric, zwitterionic, and combinations thereof;
    b. from about 0.05% to about 15%, preferably about 0.05% to about 5%, more preferably from about 0.1% to about 0.5%, by weight of the composition of a plurality of abrasive particles comprising:
      i. a mean particle size as expressed by the area-equivalent diameter from about 40 μm to about 5000 μm, preferably from about 600 μm to about 1500 μm, more preferably from about 850 μm to about 1400 μm according to ISO 9276-6:2008; and
      ii. a non-oxide colorant, preferably from about 0.05% to about 3%, more preferably from about 0.1% to about 1% by weight of the abrasive particle;
    c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
    wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and
  2. adjusting the pH of the composition to a range of 4 to 6, preferably from 5 to 6, or preferably to a pH<6.

3. The skin cleansing composition or method of examples 1 or 2, wherein the non-oxide colorant is selected from the group consisting of ultramarine blue, ferric ammonium ferrocyanide, ferric ferrocyanide, Blue No. 1 Lake, copper phthalocyanine (blue #15), yellow lake #3, yellow lake #5, yellow lake #6, red lakes, red dye #4, red dye #30, red dye #40, green #6, violet #2 and combinations thereof, preferably the non-oxide colorant is selected from the group consisting of ultramarine blue, ferric ammonium ferrocyanide, ferric ferrocyanide, Blue No. 1 Lake, copper phthalocyanine (blue #15) and combinations thereof.

4. The skin cleansing composition or method of any one of the preceding examples wherein the abrasive particles comprise stearyl stearate, candelilla wax, rice bran wax, sunflower wax, jojoba esters, carnauba wax, bees wax, corn wax, a saturated wax-ester, castor wax, ouricury wax, hydrogenated lanolin, a hydrogenated triglyceride wax, and combinations thereof, preferably the abrasive particles comprise about 1% to about 3%, by weight, of a jojoba ester, about 90% to about 95%, by weight of stearyl stearate wax; and about 4% to about 7%, by weight of candelilla wax.

5. The skin cleansing composition or method of any one of the preceding examples, the composition further comprising a viscosity from about 100 cps to about 1,000,000 cps, preferably from about 1,000 to about 300,000 cps.

6. The skin cleansing composition or method of any one of the preceding examples, wherein the surfactant is an aqueous surfactant phase; the mean particle size of the abrasive particles is from about 40 µm to about 1,400 µm; the surfactant is SLEnS where n is 0 to about 3; and further comprising a structuring material selected from the group consisting of an alkyl acrylate polymer, trihydroxystearin, and combinations thereof; and an electrolyte comprising an anion selected from the group consisting of phosphate, chloride, sulfate, citrate, and mixtures thereof, and a cation selected from the group consisting of sodium, ammonium, potassium, magnesium, and mixtures thereof, preferably the electrolyte is selected from the group consisting of sodium chloride, ammonium chloride, sodium sulfate, ammonium sulfate, and mixtures thereof.

7. The skin cleansing composition or method of any one of the preceding examples, wherein the mean particle size of the abrasive particle is from about 40 µm to about 1,400 µm; the surfactant is STnS where n is from about 0.5 to about 3; the surfactant further comprises a structuring system comprising an electrolyte and an associative polymer that is alkyl acrylate polymer; the electrolyte comprises an anion selected from the group consisting of phosphate, chloride, sulfate, citrate, and mixtures thereof, and a cation selected from the group consisting of sodium, ammonium, potassium, magnesium, and mixtures thereof, preferably the electrolyte is selected from the group consisting of sodium chloride, ammonium chloride, sodium sulfate, ammonium sulfate, and mixtures thereof.

8. The composition or method of example 7, wherein the associative polymer is selected from the group consisting of polyacrylates, hydrophobically modified polysaccharides, hydrophobically modified urethanes, and/or mixtures thereof, preferably the associative polymer comprises an alkyl acrylate polymer.

9. The composition or method of any one of the preceding examples wherein the abrasive particles are essentially free of polymer/copolymers that are selected from the group consisting of polyethylene, polypropylene, polystyrene, polyethylene terephthalate, polyester, polyurethanes, polyamides, polycarbonate, polyvinyl chloride, polyvinyl acetate, polymethyl methacrylate and copolymers, polyhydroxy alkanoate (PHA) (such as poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof), and mixtures thereof.

10. A method for cleansing a human's skin surface comprising contacting the skin surface with a skin cleansing composition according to any one of the preceding examples, and additionally followed by a rinsing step.

11. Use of abrasive particles in a skin cleansing composition according to any one of example 1, 3, 4, 5, 6, 7, 8 or 9 for delivering a benefit selected from the group consisting of mild skin exfoliation, dirt removal from a skin surface and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin cleansing composition comprising:
    a. from about 5% to about 20% by weight of the composition, of a surfactant selected from the group consisting of anionic, cationic, nonionic, amphoteric, zwitterionic, and combinations thereof;
    b. from about 0.05% to about 15%, by weight of the composition, of a plurality of abrasive particles comprising:
        i. a mean particle size as expressed by the area-equivalent diameter from about 40 µm to about 5000 µm according to ISO 9276-6:2008; and
        ii. a non-oxide colorant selected from the group consisting of ultramarine blue, ferric ammonium ferrocyanide, ferric ferrocyanide, Blue No. 1 Lake, copper phthalocyanine (blue #15), yellow lake #3, yellow lake #5, yellow lake #6, red lakes, red dye #4, red dye #30, red dye #40, green #6, violet #2 and combinations thereof;
    c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
    wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and
    wherein the skin cleansing composition comprises a pH from about 4 to about 6.

2. The skin cleansing composition of claim 1, wherein the non-oxide colorant is selected from the group consisting of ultramarine blue, ferric ammonium ferrocyanide, ferric ferrocyanide, Blue No. 1 Lake, copper phthalocyanine (blue #15) and combinations thereof.

3. The skin cleansing composition of claim 1, wherein the composition comprises from about 0.05% to about 5%, by weight of the composition of the abrasive particles.

4. The skin cleansing composition of claim 1 wherein the abrasive particles comprise stearyl stearate, candelilla wax, rice bran wax, sunflower wax, jojoba esters, carnauba wax, bees wax, corn wax, a saturated wax-ester, castor wax, ouricury wax, hydrogenated lanolin, a hydrogenated triglyceride wax, and combinations thereof.

5. The skin cleansing composition of claim 4 wherein the abrasive particles comprise about 1% to about 3%, by weight, of a jojoba ester, about 90% to about 95%, by weight of stearyl stearate wax; and about 4% to about 7%, by weight of candelilla wax.

6. The skin cleansing composition of claim 1, the composition comprising a viscosity from about 100 cps to about 1,000,000 cps.

7. The skin cleansing composition of claim 1, wherein the surfactant is an aqueous surfactant phase; the mean particle size of the abrasive particles is from about 40 μm to about 1,400 μm; the surfactant is SLEnS where n is 0 to about 3; and further comprising a structuring material selected from the group consisting of an alkyl acrylate polymer, trihydroxystrearin, and combinations thereof; and an electrolyte comprising an anion selected from the group consisting of phosphate, chloride, sulfate, citrate, and mixtures thereof, and a cation selected from the group consisting of sodium, ammonium, potassium, magnesium, and mixtures thereof.

8. The composition according to claim 7, wherein the electrolyte is selected from the group consisting of sodium chloride, ammonium chloride, sodium sulfate, ammonium sulfate, and mixtures thereof.

9. The composition according to claim 1, wherein the mean particle size of the abrasive particle is from about 40 μm to about 1,400 μm; the surfactant is STnS where n is from about 0.5 to about 3; the surfactant further comprises a structuring system comprising an electrolyte and an associative polymer that is alkyl acrylate polymer; the electrolyte comprises an anion selected from the group consisting of phosphate, chloride, sulfate, citrate, and mixtures thereof, and a cation selected from the group consisting of sodium, ammonium, potassium, magnesium, and mixtures thereof.

10. The composition according to claim 9, wherein the electrolyte is selected from the group consisting of sodium chloride, ammonium chloride, sodium sulfate, ammonium sulfate, and mixtures thereof.

11. The composition according to claim 9, wherein the associative polymer is selected from the group consisting of polyacrylates, hydrophobically modified polysaccharides, hydrophobically modified urethanes, and/or mixtures thereof.

12. The composition according to claim 11, wherein the associative polymer comprises an alkyl acrylate polymer.

13. A method of stabilizing colored abrasive particles in a skin cleansing composition, the method comprising:
  1. making a skin cleansing composition comprising:
    a. from about 5% to about 20% by weight of the composition, of a surfactant selected from the group consisting of anionic, cationic, nonionic, amphoteric, zwitterionic, and combinations thereof;
    b. from about 0.05% to about 15%, by weight of the composition, of a plurality of abrasive particles comprising:
      i. a mean particle size as expressed by the area-equivalent diameter from about 40 μm to about 5000 μm, according to ISO 9276-6:2008; and
      ii. a non-oxide colorant selected from the group consisting of ultramarine blue, ferric ammonium ferrocyanide, ferric ferrocyanide, Blue No. 1 Lake, copper phthalocyanine (blue #15), yellow lake #3, yellow lake #5, yellow lake #6, red lakes, red dye #4, red dye #30, red dye #40, green #6, violet #2 and combinations thereof;
    c. an antioxidant selected from the group consisting of tocopherol acetate (Vitamin E Acetate), butylated hydroxyanisole (BHA), butylated hydroxytoluene (BHT), sodium benzotriazolyl butylphenol sulfate, Vitamin C (ascorbic acid) and combinations thereof;
    wherein the abrasive particles are comprised of a material selected from the group consisting of: natural waxes, ester waxes, naturally-derived waxes, mineral waxes, oxides, mixed oxides, minerals, clays, carbonates, polysaccharides, sugars, starches, natural polymers, natural fibers, and combinations thereof; and
  2. adjusting the pH of the composition to a range of 4 to 6.

14. The method of claim 13, wherein the pH is from 5 to 6.

15. The method of claim 13, wherein the non-oxide colorant is selected from the group consisting of ultramarine blue, ferric ammonium ferrocyanide, ferric ferrocyanide, Blue No. 1 Lake, copper phthalocyanine (blue #15) and combinations thereof.

16. The method of claim 13, wherein the composition comprises from about 0.05% to about 5%, by weight of the composition of the abrasive particles.

17. The method of claim 13, wherein the abrasive particles comprise stearyl stearate, candelilla wax, rice bran wax, sunflower wax, jojoba esters, carnauba wax, bees wax, corn wax, a saturated wax-ester, castor wax, ouricury wax, hydrogenated lanolin, a hydrogenated triglyceride wax, and combinations thereof.

18. The method of claim 17 wherein the abrasive particles comprise about 1% to about 3%, by weight, of a jojoba ester, about 90% to about 95%, by weight of stearyl stearate wax; and about 4% to about 7%, by weight of candelilla wax.

19. The method of claim 13 wherein the composition comprises a viscosity from about 100 cps to about 1,000,000 cps.

20. The method of claim 13, wherein the surfactant is an aqueous surfactant phase; the mean particle size of the abrasive particle is from about 40 μm to about 1,400 μm; the surfactant is SLEnS where n is 0 to about 3; and further comprising a structuring material selected from the group consisting of an alkyl acrylate polymer, trihydroxystrearin, and combinations thereof; and an electrolyte comprising an anion selected from the group consisting of phosphate, chloride, sulfate, citrate, and mixtures thereof, and a cation selected from the group consisting of sodium, ammonium, potassium, magnesium, and mixtures thereof.

21. The method of claim 13, wherein the mean particle size of the structurant is from about 400 μm to about 1,400 μm; the surfactant is STnS where n is from about 0.5 to about 3; the surfactant further comprising a structuring system comprising an electrolyte and an associative polymer that is alkyl acrylate polymer; the electrolyte comprises an anion selected from the group consisting of phosphate, chloride, sulfate, citrate, and mixtures thereof, and a cation selected from the group consisting of sodium, ammonium, potassium, magnesium, and mixtures thereof.

22. A method for cleansing a human's skin surface comprising contacting the skin surface with a skin cleansing composition according to claim 1, and additionally followed by a rinsing step.

23. Use of abrasive particles in a skin cleansing composition according to claim 1 for delivering a benefit selected from the group consisting of mild skin exfoliation, dirt removal from a skin surface and combinations thereof.

24. The composition according to claim 1, wherein the plurality of abrasive particles have mean circularity of about 0.9 to about 1.0.

* * * * *